United States Patent
Ben Chaabane et al.

(10) Patent No.: US 10,030,236 B2
(45) Date of Patent: Jul. 24, 2018

(54) PROCESS FOR THE PRODUCTION OF AN ENZYMATIC COCKTAIL USING LIQUID RESIDUES FROM A PROCESS FOR THE BIOCHEMICAL CONVERSION OF LIGNOCELLULOSIC MATERIALS

(71) Applicant: IFP ENERGIES NOUVELLES, Rueil-Malmaison (FR)

(72) Inventors: Fadhel Ben Chaabane, Paris (FR); Sylvain Louret, Lyons (FR)

(73) Assignees: L'INSTITUT NATIONAL DE LA RECHERCHE AGRONOMIQUE, Paris (FR); AGRO INDUSTRIE RECHERCHES ET DEVELOPPEMENTS, Pomacle (FR)

(*) Notice: Subject to any disclaimer, the term of this patent is extended or adjusted under 35 U.S.C. 154(b) by 87 days.

(21) Appl. No.: 14/408,612

(22) PCT Filed: Jun. 10, 2013

(86) PCT No.: PCT/FR2013/051340
§ 371 (c)(1),
(2) Date: Dec. 17, 2014

(87) PCT Pub. No.: WO2013/190214
PCT Pub. Date: Dec. 27, 2013

(65) Prior Publication Data
US 2015/0152400 A1    Jun. 4, 2015

(30) Foreign Application Priority Data
Jun. 18, 2012 (FR) ..................... 12 01730

(51) Int. Cl.
*C12N 9/24* (2006.01)
*C12P 21/00* (2006.01)
*C12N 9/42* (2006.01)

(52) U.S. Cl.
CPC ......... *C12N 9/2402* (2013.01); *C12N 9/2437* (2013.01); *C12N 9/2445* (2013.01); *C12P 21/00* (2013.01); *C12P 2203/00* (2013.01); *C12Y 302/01004* (2013.01); *Y02E 50/16* (2013.01)

(58) Field of Classification Search
CPC ......... C12P 7/10; C12N 9/2437; Y02E 50/16; C12Y 302/01004; C12K 1/02; Y10S 435/945
See application file for complete search history.

(56) References Cited

U.S. PATENT DOCUMENTS

| | | |
|---|---|---|
| 2010/0267999 A1 | 10/2010 | Lau et al. |
| 2011/0236954 A1 | 9/2011 | Ben Chaabane et al. |
| 2013/0210119 A1 | 8/2013 | Ben Chaabane et al. |
| 2014/0295524 A1 | 10/2014 | Ben Chaabane et al. |

FOREIGN PATENT DOCUMENTS

| | | |
|---|---|---|
| EP | 2371950 A1 | 10/2011 |
| FR | 2962444 A1 | 1/2012 |
| FR | 2981364 A1 | 4/2013 |

OTHER PUBLICATIONS

Jae et al. Depolymerization of lignocellulosic biomass to fuel precursors: maximizing carbon efficiency by combining hydrolysis with pyrolysis. Energy Environ. Sci. 2010;3:358-365.*
International Search Report dated Nov. 8, 2013 issued in corresponding PCT/FR2013/051340 application (pp. 1-4).
M. Gyalai-Korpos et al., "Cellulase Production Using Different Streams of Wheat Grain- and Wheat Straw-Based Ethanol Processes", Journal of Industrial Microbiology & Biotechnology, vol. 38, No. 7 (2011) pp. 791-802.
L. Rosgaard et al., "Comparison of Different Pretreatment Strategies for Enzymatic Hydrolysis of Wheat and Barley Straw", Applied Biochemistry and Biotechnology, vol. 143, No. 3 (2007) pp. 284-296.
Z. Szengyel et al., "Cellulase Production Based on Hemicellulose Hydrolysate from Steam-Pretreated Willow", Applied Biochemistry and Biotechnology, vol. 63-65, No. 1 (1997) pp. 351-362.
K. Reczey et al., "Use of Hemicellulose Hydrolysate for [beta]—Glucosidase Fermentation", Applied Biochemistry and Biotechnology, vol. 70-72, No. 1 (1998) pp. 225-235.
M. Warzywoda et al., "Production and Characterization of Cellulolytic Enzymes from Trichoderma reesei Grown on Various Carbon Sources", Bioresource Technology, vol. 39, No. 2 (1992) pp. 125-130.
C.M. Lo et al., "Cellulase Production by Continuous Culture of Trichoderma reesei Rut C30 Using Acid Hydrolysate Prepared to Retain More Oligosaccharides for Induction", Bioresource Technology, vol. 101, No. 2 (2010) pp. 717-723.
R.L. Mach et al., "Regulation of Gene Expression in Industrial Fungi: Trichoderma", Applied Microbiology and Biotechnology, vol. 60, No. 5 (2003) pp. 515-522.

* cited by examiner

Primary Examiner — Lynn Y Fan
(74) Attorney, Agent, or Firm — Millen, White, Zelano & Branigan, PC

(57) ABSTRACT

A process for the production of an enzymatic cocktail with a cellulolytic microorganism comprises two phases:
a phase a) for growth of said microorganism in a closed reactor in the presence of a carbonaceous growth solution;
a phase b) for the production of said enzymatic cocktail carried out with a supply of carbonaceous production solution the concentration of carbonaceous substrate of which is in the range 150 to 400 g/L, said carbonaceous production solution comprising a carbonaceous inducer substrate;
characterized in that said carbonaceous inducer substrate is a liquid residue obtained from a step for pre-treatment of lignocellulosic materials, the $C_5$ sugar oligomers of which represent at least 1% by weight of the total sugars present in said liquid residue, and at least 0.3% by weight of the total sugars present in said carbonaceous production solution.

11 Claims, No Drawings

PROCESS FOR THE PRODUCTION OF AN ENZYMATIC COCKTAIL USING LIQUID RESIDUES FROM A PROCESS FOR THE BIOCHEMICAL CONVERSION OF LIGNOCELLULOSIC MATERIALS

FIELD OF THE INVENTION

The present invention relates to the production of cellulolytic and hemicellulolytic enzymes, in particular in the context of the production of ethanol from cellulosic or lignocellulosic materials.

PRIOR ART

Since the 1970s, the transformation of lignocellulosic materials into ethanol after hydrolysis of the constituent polysaccharides into fermentable sugars has been the focus of a great many studies. Examples which may be studied are the reference works from the National Renewable Energy Laboratory (Process Design and Economics for Biochemical Conversion of Lignocellulosic Biomass to Ethanol, Humbird et al., NREL/TP-5100-57764, May 2011).

Lignocellulosic materials are cellulosic materials, i.e. constituted by more than 90% by weight of cellulose and/or lignocellulose, i.e. constituted by cellulose, hemicelluloses, which are polysaccharides essentially constituted by pentoses and hexoses as well as lignin, which is a macromolecule with a complex structure and a high molecular weight based on phenolic compounds.

Wood, straw and corn cobs are the most widely used lignocellulosic materials, but other sources, dedicated forest cultures, residues of alcoholigenic sugar and cereal plants, products and residues from the papermaking industry and transformation products of lignocellulosic materials may be used. They are mostly constituted by approximately 35% to 50% of cellulose, 20% to 30% of hemicellulose and 15% to 25% of lignin.

The process for the biochemical transformation of lignocellulosic materials into ethanol comprises a step for physico-chemical pre-treatment followed by a step for enzymatic hydrolysis using an enzymatic cocktail, by a step for ethanolic fermentation of the liberated sugars, the ethanolic fermentation and enzymatic hydrolysis possibly being carried out simultaneously, and by a step for purification of the ethanol.

The enzymatic cocktail is a mixture of cellulolytic enzymes (also known as cellulases) and/or hemicellulolytic enzymes. The cellulolytic enzymes have three main types of activities: endoglucanases, exoglucanases and cellobiases, these latter also being known as β-glucosidases. The hemicellulolytic enzymes in particular have xylanase activities.

Enzymatic hydrolysis is efficient and is carried out under mild conditions. In contrast, the cost of enzymes is still high, representing 20% to 50% of the cost of transforming lignocellulosic material into ethanol. For this reason, a great many studies have been carried out concerning reducing this cost: optimization of enzyme production initially, by selecting hyperproductive microorganisms and by improving the processes for producing said enzymes, reducing the quantity of enzymes in hydrolysis then, by optimizing the pre-treatment step, by improving the specific activity of these enzymes, and by optimizing the implementation of the enzymatic hydrolysis step.

During the past decade, a great many studies have been aimed at understanding the mechanisms of action and the expression of the enzymatic cocktail. The aim is to cause that cocktail to be excreted which is the most appropriate to hydrolysis of the lignocellulosic materials by modifying the microorganisms.

The cellulolytic microorganism which is the most widely used for the industrial production of the enzymatic cocktail is the fungus *Trichoderma reesei*. In the presence of an inducer carbonaceous substrate, for example cellulose, wild strains have the ability to excrete the enzymatic cocktail considered to be the most suitable for hydrolysis of the cellulose. Other proteins having properties which are indispensable to the hydrolysis of lignocellulosic materials are also produced by *Trichoderma reesei*, for example xylanases. The presence of an inducer substrate is indispensable to the expression of cellulolytic and/or hemicellulolytic enzymes. The nature of the carbonaceous substrate has a considerable influence on the composition of the enzymatic cocktail. This is the case with xylose which, when associated with a carbonaceous inducer substrate such as cellulose or lactose, can significantly improve the activity termed xylanase activity.

Lactose remains one of the most appropriate substrates in the industrial process for the production of enzymatic cocktail; however, its cost varies widely and represents approximately one to two thirds of the cost price of the enzymes. When lactose is used as the carbonaceous substrate, the enzymatic cocktail production process is dependent on an external source of carbon. For this reason, the use of carbonaceous substrates obtained from a process for the biochemical conversion of lignocellulosic materials constitutes a major advance.

Patent application EP 1 690 944 discloses that the extract from the hemicellulosic fraction in the monomeric form deriving from pre-treated lignocellulosic materials may be used as a non-inducer carbonaceous substrate for the growth of the cellulolytic microorganism and the production of enzymes. In this latter case, it has to be mixed with an inducer carbonaceous substrate for the production of cellulases (lactose or cellobiose).

Patent applications WO 09 026 716 A1 and WO 09 0061486 A1 describe the production of an enzymatic cocktail from *Trichoderma reesei* using a carbonaceous substrate containing inducer sugars for the production of cellulases as well as a principal source of carbon. This application discloses that 3% by weight of inducer sugars are sufficient to induce the production of cellulases. The production of cellulases is multiplied by a factor of more than 4 compared with the example in which xylose is used alone in the production solution. The inducer sugars described are mono-, di- and oligo-saccharides ($C_6$ sugars) possibly produced by the hydrolysis of cellulose. The principal source of carbon is an ensemble comprising mono-, di- and oligosaccharides obtained from hemicelluloses or from synthetic xylose.

The document FR 2 962 444 discloses a process for the production of cellulolytic and/or hemicellulolytic enzymes. The inducer substrate is a mixture of glucose or cellulosic hydrolysates, lactose and xylose or a solution of hemicellulosic hydrolysates with at least 10% by weight of each of these three groups of constituents. That document indicates that the inducer substrate is free from any other sugar other than the constituents listed above, the cellulosic hydrolysates being glucose obtained from the hydrolysis of cellulose, and the hemicellulosic hydrolysates being a solution of $C_5$ sugars.

The document EP 2 371 950 A1 describes a process for the production of cellulases based on regulating the swing of the oxygen pressure dissolved in the culture medium. That document discloses that the carbonaceous inducer substrate is selected from lactose, xylose, cellobiose, sophorose, residues obtained after fermenting monomer sugars and/or a crude extract of hydrosoluble pentoses, i.e. hydrosoluble $C_5$ sugars.

The publication "Cellulase Production by Continuous Culture of *Trichoderma reesei* Rut C30 using acid hydrolysate prepared to retain more oligosaccharides for induction", Lo et al., Bioresource Technology 101 (2010) 717-723, teaches induction by the oligosaccharides produced by acid hydrolysis of cellulose, said hydrolysate, constituted by $C_6$ sugar oligomers, being rendered basic by a solution of $Ca(OH)_2$ before being neutralized. The role of inducer played by the $C_6$ oligomers, in particular cellobiose, is also known.

One aim of the invention is to propose a novel source of inducer carbon which is readily available, which can produce an enzymatic cocktail with activities appropriate for hydrolysis of the lignocellulosic material. Compared with patent EP 1 690 944, the invention claims the advantageous use of a hemicellulosic fraction also containing oligomers, which means that the addition of an inducer substrate can be dispensed with. Compared with patent WO 09 026716, the invention recommends the use of a single source of non-synthetic carbon which is particularly suited to the expression of a mixture of enzymes which is entirely effective for the treatment of the biomass to be hydrolysed. That invention also enables the co-products to be upgraded internally.

SUMMARY AND ADVANTAGE OF THE INVENTION

The present invention concerns a process for the production of an enzymatic cocktail by a cellulolytic microorganism, characterized in that it uses a liquid residue from the pre-treatment of lignocellulosic materials as an inducer carbonaceous substrate for inducing the production of enzymatic cocktail.

One advantage of the invention is to reduce or dispense with the addition of carbonaceous substrate of external origin to the biochemical process for the conversion of lignocellulosic materials. Another advantage is that liquid residues from said biochemical conversion process for the production of an enzymatic cocktail are upgraded. Upgrading in this manner means that the quantity of effluents produced which have to be re-treated before discharge or storage can be reduced.

Since liquid residues containing inducer oligomers are upgraded to produce an enzymatic cocktail, the cost of said cocktail is reduced.

An additional advantage of the process of the invention is that an enzymatic cocktail is produced which is particularly suitable for enzymatic hydrolysis of the pre-treated lignocellulosic material converted in the biochemical conversion process. In particular, a positive effect of $C_5$ oligomers on the cellulase activity of the enzymes obtained has been discovered.

DETAILED DESCRIPTION OF THE INVENTION

The present invention is a process for the production of an enzymatic cocktail with a cellulolytic microorganism, comprising two phases:

a phase a) for growth of said microorganism in a closed reactor in the presence of a carbonaceous growth solution;

a phase b) for the production of said enzymatic cocktail carried out with a supply of carbonaceous production solution the concentration of carbonaceous substrate of which is in the range 150 to 400 g/L, said carbonaceous production solution comprising a carbonaceous inducer substrate;

characterized in that said carbonaceous inducer substrate is a liquid residue obtained from a step for pre-treatment of lignocellulosic materials used without sterilization or modification of the pH of said liquid residue, the $C_5$ sugar oligomers of which represent at least 1% by weight of the total sugars present in said liquid residue, and at least 0.3% by weight of the total sugars present in said carbonaceous production solution.

Preferably, the carbonaceous growth solution used in said phase a) is at an initial concentration in the range 10 to 90 g of carbonaceous substrate per liter of reaction volume.

Preferably, said pre-treatment step is acid hydrolysis, acid cooking or steam explosion with prior impregnation of said lignocellulosic materials with an aqueous sulphuric acid solution.

Preferably, said liquid residue is used with neither sterilization nor modification of the pH of said liquid residue. More preferably, said liquid residue is used with neither sterilization nor detoxification, nor modification of the pH of said liquid residue.

Preferably, the $C_5$ sugar oligomers represent in the range 1% to 50% by weight of the total sugars present in said liquid residue.

Preferably, said inducer carbonaceous substrate is used alone or as a mixture with at least one other non-inducer carbonaceous substrate.

Preferably, said other non-inducer carbonaceous substrate is selected from glucose, xylose, and saccharose, alone or as a mixture.

Preferably, said carbonaceous production solution consists of a liquid residue and at least one non-inducer carbonaceous substrate selected from glucose, xylose and saccharose, alone or as a mixture, said liquid residue being obtained from a step for pre-treatment of lignocellulosic materials, and used with neither sterilization nor detoxification nor modification of the pH, said liquid residue consisting of $C_5$ sugar oligomers, of $C_5$ and $C_6$ sugar monomers and of sugar monomer degradation products, wherein the $C_5$ sugar monomers represent at least 1% by weight of the total sugars present in said liquid residue, and at least 0.3% by weight of the total sugars present in said carbonaceous production solution.

Preferably, the specific flow rate for supplying carbonaceous production solution for phase b) is in the range 35 to 65 mg of carbonaceous substrate per gram of microorganism per hour.

Preferably, the cellulolytic microorganism is selected from strains of fungi belonging to the genera *Trichoderma, Aspergillus, Penicillium* or *Schizophyllum*.

Preferably, the cellulolytic microorganism belongs to the species *Trichoderma reesei*.

Said process for the production of an enzymatic cocktail is carried out using submerged culture. The term "submerged culture" means culture in a liquid medium.

The cellulolytic microorganisms used in the process for the production of an enzymatic cocktail of the invention are strains of cellulolytic fungi, for example belonging to the genera *Trichoderma, Aspergillus, Penicillium* or *Schizophyllum*, preferably belonging to the species *Trichoderma reesei*. The best performing industrial strains are strains belonging to the species *Trichoderma reesei*, modified to improve the enzymatic cocktail by mutation-selection processes such as, for example, the strain IFP CL847 (French patent FR-B-2 555 803). Strains improved by genetic recombination techniques may also be used. These strains are cultivated in stirred, aerated reactors under conditions compatible with their growth and the production of enzymes.

The term "carbonaceous substrate" means all of the sugars comprised in the carbonaceous solution.

The carbonaceous growth substrate for said microorganism used in said phase a) of the process of the invention is an aqueous solution advantageously comprising a carbonaceous substrate selected from soluble industrial sugars, preferably from glucose, xylose, liquid residues obtained after ethanolic fermentation of sugar monomers from enzymatic hydrolysates of lignocellulosic materials and extracts from the hemicellulosic fraction in the form of monomers obtained from pre-treated lignocellulosic materials, used alone or as a mixture. Depending on its nature, said carbonaceous growth solution is introduced into the closed reactor before sterilization or is sterilized separately and introduced into the closed reactor after sterilization of the latter.

Preferably, said carbonaceous growth solution is used in said phase a) at an initial concentration in the range 10 to 90 g of carbonaceous substrate per liter of reaction volume.

Preferably, said phase a) is carried out for a period in the range 30 to 70 h, preferably in the range 30 to 40 h.

Preferably, said phase a) is operated at a pH of 4.8 and at a temperature of 27° C.

Preferably, said phase a) is carried out in a closed, aerated and stirred reactor. Aeration is adjusted so as to obtain a VVM (volume flow rate of air, $Nm^3$/min, divided by the reaction volume in $m^3$) in the range 0.1 to 1, preferably in the range 0.3 to 0.7, and more preferably in order to obtain a VVM of 0.5. Stirring is adapted so as to obtain a partial pressure of dissolved oxygen in the range 20% to 80% of the theoretical saturation, preferably in the range 30% to 50%, and more preferably a value of 40%.

The carbonaceous solution for production of said microorganism used in said phase b) of the invention is an aqueous solution comprising an inducer carbonaceous substrate. Said inducer carbonaceous substrate is a liquid residue obtained from the step for pre-treatment of the lignocellulosic materials comprising $C_5$ sugar oligomers.

In accordance with the invention, said $C_5$ sugar oligomers represent at least 0.3% by weight of the total sugars contained in said carbonaceous production solution. Preferably, said $C_5$ sugar oligomers represent in the range 0.3% to 50% by weight of the total sugars contained in said carbonaceous production solution, preferably in the range 0.3% to 20% by weight, more preferably in the range 0.3% to 10% by weight and still more preferably in the range 0.3% to 6% by weight.

Preferably, said inducer carbonaceous substrate is used alone or as a mixture with at least one other non-inducer carbonaceous substrate.

Preferably, said other non-inducer carbonaceous substrate is selected from non-inducer sugars, preferably selected from glucose, saccharose and xylose, alone or as a mixture. Highly preferably, said other carbonaceous substrate is selected from glucose and saccharose, alone or as a mixture.

In accordance with the invention, said carbonaceous production solution used in said phase b) of the invention is prepared at a concentration of 150 to 400 g of carbonaceous substrate per liter of carbonaceous production solution. The specific flow rate for supplying carbonaceous production solution for said phase b) is advantageously in the range 35 to 65 mg of carbonaceous substrate per gram of microorganism per hour, preferably 35 to 45 mg of carbonaceous substrate per gram of microorganism per hour.

Preferably, said phase b) is carried out for a period of at least 30 h or more, preferably at least 100 h or more.

Preferably, said phase b) is operated at a pH in the range 3 to 5.5 and at a temperature in the range 20° C. to 30° C.

Preferably, said phase b) is carried out in an aerated and stirred reactor. Aeration is adjusted so as to obtain a VVM in the range 0.1 to 1, preferably in the range 0.3 to 0.7, and more preferably so as to obtain a VVM of 0.5. Stirring is adapted so as to obtain a partial pressure of dissolved oxygen in the range 20% to 80%, preferably in the range 30% to 50%, and more preferably a value of 40%.

Said phase b) may be carried out in accordance with fed-batch and chemostat modes which are known to the skilled person.

The $C_5$ sugar oligomers used as the inducer carbonaceous substrate in the carbonaceous production solution used in said phase b) are comprised in a liquid residue obtained from the step for pre-treatment of the lignocellulosic materials.

Said step for pre-treatment of lignocellulosic material can be used to improve the susceptibility of the cellulosic fraction to enzymatic hydrolysis. Said pre-treatment step is a physical pre-treatment step such as, for example, a steam explosion step, or a chemical or physico-chemical step. Preferably, said pre-treatment step is an acidic or basic pre-treatment step such as, for example, alkaline hydrolysis, alkaline cooking or steam explosion with prior impregnation of said material with an aqueous alkaline solution. Preferably, said pre-treatment step is an acid pre-treatment step, preferably acid hydrolysis, acid cooking or steam explosion with prior impregnation of said material with an aqueous sulphuric acid solution. Highly preferably, the pre-treatment step is steam explosion.

The effluent from said pre-treatment step is separated into two phases: a phase constituting the solid residue and a phase constituting the liquid residue. Said separation may be obtained by any means known to the skilled person. As an example, said separation may be obtained by centrifuging, a filter press, decanting, or any other technical means allowing separation of a liquid phase and a solid phase.

In the case of an acid pre-treatment, the skilled person adjusts the operating conditions (quantity of acid, humidity, temperature, pressure, duration) as a function of the lignocellulosic material to be pre-treated and the technologies employed. Said operating conditions will be more severe for miscanthus than for wheat straw, for example. These adjustments are intended to result in complete hydrolysis of the hemicelluloses in the form of monomers, while minimizing the formation of degradation products (in particular furfural, 5-HMF). To this end, the pre-treatment step may also be subdivided into two phases: a first phase for liberating $C_5$ sugar oligomers, followed by a phase for producing monomers from the liberated oligomers (Process Design and Economics for Biochemical Conversion of Lignocellulosic Biomass to Ethanol, Humbird et al., NREL/TP-5100-57764, May 2011).

In accordance with the invention, said pre-treatment step is operated using means which are known to the skilled person such that the liquid residue comprises $C_5$ sugar oligomers.

In order to obtain the $C_5$ sugar oligomers in the liquid residue from said pre-treatment step, the quantity of acid employed in said pre-treatment step can be reduced. It is also possible to reduce the temperature and/or the pressure at which said pre-treatment step is operated compared with optimized conditions so as to liberate only the monomers.

In accordance with the invention, said $C_5$ sugar oligomers comprised in said liquid residue obtained from the step for pre-treatment of lignocellulosic materials represent between 1% and 100% by weight of the total sugars present in said liquid residue, preferably in the range 1% to 50% by weight, and more preferably in the range 1% to 30% by weight.

Said liquid residue containing the $C_5$ sugar oligomers obtained from said pre-treatment step is used as a source of inducer carbon without the need to either sterilize said liquid residue or modify the pH of said residue.

In a preferred embodiment, the pre-treated lignocellulosic material which corresponds to the fraction termed "solid" is hydrolysed in an enzymatic hydrolysis step. The effluent from this step is then treated in a step for ethanolic fermentation of the sugar monomers of the enzymatic hydrolysates. These treatments may be carried out in the same equipment, or in different equipment.

In another preferred embodiment, the fermentation step and at least a portion of the hydrolysis step are carried out simultaneously. This is accomplished, for example, by adding ethanolic yeasts during the enzymatic hydrolysis step.

The following examples illustrate the invention without limiting its scope.

Example 1 (not in Accordance with the Invention): Production of an Enzymatic Cocktail on Glucose Example 1 presents a culture using glucose as the carbonaceous production substrate. It is a repressor of cellulase production. This example resulted in a low production of enzymes.

An enzymatic cocktail was produced in a mechanically stirred reactor. The mineral medium (termed 4N) had the following composition: KOH 1.66 g/L, 85% $H_3PO_4$ 2 mL/L, $(NH_4)_2SO_4$ 2.8 g/L, $MgSO_4 \cdot 7 H_2O$ 0.6 g/L, $CaCl_2$ 0.6 g/L, $MnSO_4$ 3.2 mg/L, $ZnSO_4 \cdot 7 H_2O$ 2.8 mg/L, $CoCl_2 \cdot 10 H_2O$ 4.0 mg/L, $FeSO_4 \cdot 7 H_2O$ 10 mg/L, Corn Steep 1.2 g/L, anti-foaming agent 0.5 mL/L.

Liquid Preculture

The microorganism (the *Trichoderma reesei* CL847 strain) was grown, by preculture using glucose as the carbonaceous growth substrate, at a concentration of 30 g/L. The mineral medium of the preculture was the 4N medium supplemented with 5 g/L potassium phthalate in order to buffer the pH. Inoculum growth lasted 3 days and was carried out at 30° C. in a stirred incubator. Transfer to the reactor was carried out if the residual glucose concentration was less than 15 g/L.

Growth Phase

The reactor containing the 4N medium was sterilized at 120° C. for 20 minutes. The glucose carbonaceous growth substrate was sterilized from 120° C. for 20 minutes then added to the reactor in a sterile manner so as to produce a concentration of 30 g/L. The reactor was inoculated to 10% (v/v) with the liquid preculture of the *Trichoderma reesei* CL847 strain. The operating conditions were a temperature of 27° C. and a pH of 4.8 (regulated using 5.5 mol/L ammonia). Aeration was at 0.5 VVM and stirring was increased to between 200 and 800 rpm as a function of the $pO_2$ (pressure of dissolved oxygen), which was maintained at 30%.

Production Phase

When the carbonaceous growth substrate of the reactor was exhausted, the 250 g/L glucose carbonaceous production substrate was injected continuously at a flow rate of 35 to 45 mg per g of microorganism per hour, for 164 hours. The operating conditions were: a temperature of 25° C. and a pH of 4 (regulated with 5.5 mol/L ammonia, this latter also providing the nitrogen necessary for synthesis of the excreted proteins). The dissolved oxygen content was maintained at 30% by adjusting the stirring.

Production of the enzymes was monitored by assaying extracellular enzymes using the Lowry method and standard BSA after separating out the microorganism by filtering or centrifuging. The cellulolytic activities which were determined were as follows:

filter paper activity (FPU: filter paper unit) in order to assay the overall activity of the endoglucanase and exoglucanase enzymatic cocktail;

the aryl β-glucosidase activity for the specific activities.

The FPU activity was measured on Whatman no. 1 paper (procedure recommended by the IUPAC biotechnological commission) at an initial concentration of 50 g/L; the sample of enzymatic solution to be analysed which liberated the equivalent of 2 g/L of glucose (colorimetric assay) in 60 minutes was determined. The principle of filter paper activity is to determine the quantity of reduced sugars obtained from a Whatman n° 1 paper by DNS assay (dinitrosalicylic acid) (procedure recommended by the IUPAC biotechnological commission).

The substrate used to determine the aryl β-glucosidase activity was p-nitrophenyl-β-D-glucopyranoside (PNPG). It is cleaved by β-glucosidase which liberates p-nitrophenol.

One aryl β-glucosidase activity unit is defined as the quantity of enzyme necessary to produce 1 μmol of p-nitrophenol from PNPG per minute and is expressed in IU/ml.

The specific activities are obtained by dividing the activities, expressed in IU/ml, by the concentration of proteins. They are expressed in IU/mg.

The analytical determinations on the final mash of Example 1 gave the following results:

| | |
|---|---|
| Biomass g/L | 15.2 |
| Enzymes g/L | 2.9 |
| FPU IU/mL | 1.4 |
| Specific aryl β-glucosidase IU/mg | 0.35 |

Example 2 (not in Accordance with the Invention): Production of Enzymes on Xylose Example 2 presents a culture using xylose as the carbonaceous production substrate. It is a repressor of cellulase production. This example resulted in a low production of enzymes.

The enzymes were produced under the same conditions as in Example 1. The carbonaceous substrate during the growth phase was lactose and during the production phase, it was pure xylose.

After 30 hours growth, after exhausting the initial substrate, the 250 g/L xylose solution was injected continuously at a flow rate of 35 mg per g of cells per hour, for 164 hours.

The analytical determinations carried out on the final mash provided the following results:

| | |
|---|---|
| Biomass g/L | 17.3 |
| Enzymes g/L | 3.1 |
| FPU IU/mL | 1.2 |
| Specific aryl β-glucosidase IU/mg | 0.1 |

Example 3 (not in Accordance with the Invention): Production of Enzymes on Lactose Example 3 presents a culture using lactose as the carbonaceous production substrate. It is an inducer of cellulase production. This example results in a high production of high activity enzymes.

The enzymes were produced under the same conditions as in Example 1. The carbonaceous substrate during the growth phase and the production phase was pure lactose. Lactose is an important inducer of cellulase production. It is the most widely used industrial substrate for the production of cellulases.

After 30 hours growth, after exhausting the initial substrate, the 250 g/L fed batch solution was injected continuously at a flow rate of 35 mg per g of cells per hour, for 164 hours.

The analytical determinations carried out on the final mash provided the following results:

| | |
|---|---|
| Biomass g/L | 13.5 |
| Enzymes g/L | 37.8 |
| FPU IU/mL | 22.1 |
| Specific aryl β-glucosidase IU/mg | 0.96 |

Example 4 (in Accordance with the Invention): Production on 100% Liquid Residue Containing $C_5$ Sugar Oligomers Example 4 presents a culture using the liquid residue as the carbonaceous production substrate. This example resulted in a production of enzymes and an activity which was higher than that obtained in Examples 1 and 2. It thus shows that the liquid residue used alone induces the production of cellulases. It results in an effect similar to that which is described in the patent WO 09 026 716 A1, but without the addition of inducer solution other than the liquid residue.

Enzyme production was carried out under the same conditions as in Example 1. The carbonaceous substrate during the growth phases was glucose. The carbonaceous substrate during the production phase was the liquid fraction obtained after pre-treatment, known as "a liquid residue". This was obtained from a miscanthus pre-treated by steam explosion at 14.5 bar for 2 minutes after impregnation with 0.65% $H_2SO_4$ then liquid phase/solid phase separation.

Its composition was as follows:

| | |
|---|---|
| Oligomers | 0.78 g/L |
| Glucose | 8.98 g/L |
| Xylose | 31.44 g/L |
| Galactose | 1.73 g/L |
| Arabinose | 3.85 g/L |
| Acetic acid | 4.14 g/L |
| HMF | 0.14 g/L |
| Furfural | 0.85 g/L |
| Total | 51.91 g/L |

It was concentrated to 300 g/L. After 30 hours growth, after exhausting the initial substrate, the concentrated hemicellulosic hydrolysate was injected continuously at a flow rate of 35 mg per g of cells per hour.

The analytical determinations on the final mash provided the following results:

| | |
|---|---|
| Biomass g/L | 26.0 |
| Enzymes g/L | 19.2 |
| FPU IU/mL | 4.9 |
| Specific aryl β-glucosidase IU/mg | 0.48 |

Example 5 (in Accordance with the Invention): Production on Two Different Liquid Residues Comprising Different Proportions of Oligomers Example 5 presents two cultures each using the liquid residue as the carbonaceous production substrate. This example resulted in a production of enzymes and an activity which was higher than that obtained in Examples 1 and 2. It shows that the $C_5$ sugar oligomers content has a positive effect on the quantity and activity of the enzymes obtained.

Two distinct liquid residues were obtained from steam exploded wheat straw. The operating conditions for the steam explosion were 14.5 bar for 2 minutes. The liquid residue C1 was obtained from wheat straw which had already been impregnated with 0.64% $H_2SO_4$. The liquid residue C2 was obtained from wheat straw which had already been impregnated with 0.32% $H_2SO_4$.

The liquid residue C2 contained a higher proportion of oligomers obtained from the hydrolysis of hemicelluloses from the straw compared with the hydrolysate C1 due to the smaller quantity of acid used for impregnation of the wheat straw.

The composition of liquid residues C1 and C2 is detailed in the table below:

| | C1 | C2 |
|---|---|---|
| Monomers | 50.9 g/L | 33.6 g/L |
| Oligomers | 0.9 g/L | 14.1 g/L |
| Degraded sugars | 2.9 g/L | 1.8 g/L |
| TOTAL | 54.7 g/L | 49.5 g/L |

The monomers correspond to the sum of glucose, xylose, arabinose, mannose, galactose and rhamnose. The oligomers correspond to the sum of the $C_5$ sugar oligomers (for example: xylobiose, xylotriose, xyloarabinose). The degraded sugars correspond to the sum of furfural, 5HMF, levulinic acid and formic acid.

Two fed batch solutions were prepared by dissolving glucose in the C1 and C2 hydrolysates in order to obtain a total sugar concentration of 250 g/L. Glucose is a repressor of cellulase production.

The experiments were carried out under the same conditions as in Example 1.

The analytical determinations on the final mash obtained provided the following results:

| | Fed-batch C1 | Fed-batch C2 |
|---|---|---|
| Biomass g/L | 24.8 | 19.2 |
| Enzymes g/L | 20.9 | 32.9 |
| FPU IU/mL | 11.4 | 15.6 |
| aryl β-Glucosidase IU/mL | 45.2 | 65.1 |

The fed batch solution C2, which contained more oligomers obtained from the hemicellulose fraction, resulted in production of more proteins than that of the fed batch solution C1 with better enzymatic activities. In this example, enzyme production was carried out with carbon sources potentially obtained only from the process for the production of ethanol from lignocellulosic biomass, the glucose possibly being replaced by a cellulosic hydrolysate.

Example 6 (not in Accordance with the Invention)—Production on Liquid Residue (Hemicellulolytic Hydrolysate) Containing No $C_5$ Sugar Oligomers Example 6 shows that, starting from the liquid residue C2 of Example 5, it is indeed the $C_5$ sugar oligomers which induce the production of enzymes The solution C2 of Example 5 initially underwent acid hydrolysis in order to hydrolyse the oligomers to monomers. The composition of the new solution C3 was as follows:

|  | C3 |
| --- | --- |
| Monomers | 45.7 g/L |
| Oligomers | 0.0 g/L |
| Degraded sugars | 3.5 g/L |
| TOTAL | 49.2 g/L |

The same conditions as in Example 5 were used for culture. A fed batch solution was prepared by dissolving glucose in C3 so as to obtain a total concentration of sugars of 250 g/L. The analytical determinations on the final mash produced the following results:

| Biomass g/L | 21.2 |
| --- | --- |
| Enzymes g/L | 3.9 |
| FPU IU/mL | 1.1 |
| aryl β-Glucosidase IU/mg | 0.2 |

This example shows that in the absence of hemicellulosic oligomers, the liquid residues do not induce the production of cellulases.

The invention claimed is:

1. A process for the production of an enzymatic cocktail with a cellulolytic microorganism, comprising:
   pre-treating lignocellulosic materials without sterilization or modification of the pH of a liquid residue obtained therefrom,
   growing a microorganism in a closed reactor in the presence of a carbonaceous growth solution comprising a carbonaceous growth substrate;
   producing an enzymatic cocktail comprising a supply of carbonaceous production solution including a concentration of a carbonaceous substrate in the range 150 to 400 g/L, wherein the carbonaceous production solution comprises a carbonaceous inducer substrate, wherein the carbonaceous inducer substrate is the obtained liquid residue and comprises $C_5$ sugar oligomers,
   wherein the $C_5$ sugar oligomers are at least 1% by weight of the total sugars present in said liquid residue, and are 0.3% to 20% by weight of the total sugars present in said carbonaceous production solution wherein the $C_5$ sugar oligomers in the carbonaceous inducer substrate induce the production of enzymes.

2. The process of claim 1, wherein in the growing step the carbonaceous growth solution is present in an initial concentration of 10 to 90 g of carbonaceous substrate per liter of reaction volume.

3. The process of claim 1, wherein said pre-treatment step is acid hydrolysis, acid cooking, or steam explosion with prior impregnation of said lignocellulosic materials with an aqueous sulphuric acid solution.

4. The process of claim 1, wherein said liquid residue is not detoxified.

5. The process of claim 1, wherein the $C_5$ sugar oligomers are 1% to 50% by weight of the total sugars present in said liquid residue.

6. The process of claim 1, wherein said carbonaceous inducer substrate is used alone or as a mixture with at least one non-inducer carbonaceous substrate.

7. The process of claim 6, wherein said non-inducer carbonaceous substrate is glucose, xylose or saccharose, alone or as a mixture.

8. The process of claim 1, wherein said carbonaceous production solution consists of the carbonaceous inducer substrate and at least one non-inducer carbonaceous substrate which is glucose, xylose or saccharose, alone or as a mixture,
   wherein said liquid residue is obtained without detoxification of said liquid residue, and consists of $C_5$ sugar oligomers, $C_5$ and $C_6$ sugar monomers, and sugar monomer degradation products.

9. The process of claim 1, wherein a specific flow rate for supplying carbonaceous production solution is in the range 35 to 65 mg of carbonaceous inducer substrate per gram of microorganism per hour.

10. The process of claim 1, wherein the cellulolytic microorganism is strains of *Trichoderma, Aspergillus, Penicillium* or *Schizophyllum*.

11. The process of claim 10, wherein the cellulolytic microorganism is strains of *Trichoderma reesei*.

* * * * *